United States Patent
Tets et al.

(10) Patent No.: US 8,993,712 B2
(45) Date of Patent: Mar. 31, 2015

(54) METHOD FOR PRODUCING BIOCIDAL POLYGUANIDINE, AND BIOCIDAL POLYGUANIDINE

(75) Inventors: Viktor Veniaminovich Tets, Saint-Petersburg (RU); Georgy Viktorovich Tets, Saint-Petersburg (RU); Konstantin Andreevich Krasnov, Saint-Petersburg (RU)

(73) Assignees: Viktor Veniaminovich Tets, Saint-Petersburg (RU); Georgy Viktorovich Tets, Saint-Petersburg (RU)

( * ) Notice: Subject to any disclaimer, the term of this patent is extended or adjusted under 35 U.S.C. 154(b) by 804 days.

(21) Appl. No.: 13/142,760

(22) PCT Filed: Jun. 4, 2010

(86) PCT No.: PCT/RU2010/000292
§ 371 (c)(1),
(2), (4) Date: Jun. 29, 2011

(87) PCT Pub. No.: WO2011/043690
PCT Pub. Date: Apr. 14, 2011

(65) Prior Publication Data
US 2011/0269936 A1   Nov. 3, 2011

(30) Foreign Application Priority Data
Oct. 8, 2009 (RU) .................. 2009137333

(51) Int. Cl.
 C08G 73/02  (2006.01)
 A61K 31/155  (2006.01)
 A61K 31/785  (2006.01)
 C07C 281/16  (2006.01)
 C08G 73/00  (2006.01)

(52) U.S. Cl.
 CPC ............. *A61K 31/155* (2013.01); *A61K 31/785* (2013.01); *C07C 281/16* (2013.01); *C08G 73/00* (2013.01)
 USPC .......................................... 528/422; 528/486

(58) Field of Classification Search
 CPC ....................................................... C08G 73/02
 USPC ................................................. 528/422, 486
 See application file for complete search history.

(56) References Cited

FOREIGN PATENT DOCUMENTS

| RU | 2039735 | 7/1995 |
| RU | 2141452 | 11/1999 |
| RU | 2176523 | 12/2001 |
| RU | 2176651 | 12/2001 |
| RU | 2230734 | 6/2004 |
| RU | 2006122738 | 1/2008 |
| RU | 2324478 | 5/2008 |

OTHER PUBLICATIONS

Supplementary European Search Report dated Nov. 20, 2013, from corresponding European Application No. 10 82 2298.
Translation of the International Preliminary Report on Patentability dated Apr. 11, 2012 from corresponding International Application No. PCT/RU2010/000292.
Translation of the International Search Report dated Oct. 28, 2010, from corresponding International Application No. PCT/RU2010/000292.
Translation of the Written Opinion of the International Searching Authority dated Oct. 28, 2010, from corresponding International Application No. PCT/RU2010/000292.
Dafu Wei, et al. "Structural characterization and antibacterial activity of oligoguanidine (polyhexamethylene guanidine hydrochloride)" 2009, Materials Science and Engineering, vol. 29, No. 6, pp. 1776-1780.

*Primary Examiner* — Duc Truong
(74) *Attorney, Agent, or Firm* — Troutman Sanders LLP

(57) ABSTRACT

The inventions relate to antiseptic agents and the method for producing thereof and can be used as a broad-spectrum disinfectant in medicine, veterinary medicine, agriculture etc.
The method for producing of biocidal polyguanidine that comprises condensation polymerization of hexamethylenediamine with guanine salt additionally uses hydrazine hydrate during the condensation polymerization process, at the following ratio of components, mass %:
 hexamethylenediamine 20-55
 guanidine salt 25-65
 hydrazine hydrate the rest.
Biocidal polyguanidine obtained by means of the abovementioned method, with the following formula:

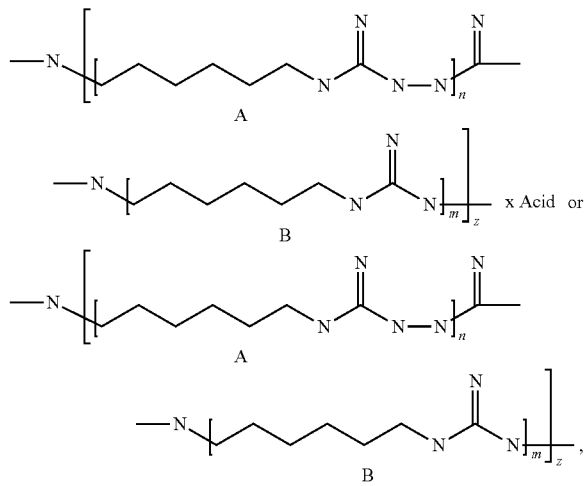

where
 n—the number of links A in a single unit of the polymer chain, n=1-3;
 m—the number of links B in a single unit of the polymer chain, m=2-10;
 z—the number of single units in the polymer chain, z=4-20;
 Acid—an acid.
The inventions allow obtaining a biocidal polyguanidine with high level of broad-spectrum antimicrobial activity.

36 Claims, No Drawings

METHOD FOR PRODUCING BIOCIDAL POLYGUANIDINE, AND BIOCIDAL POLYGUANIDINE

CROSS REFERENCE TO RELATED APPLICATIONS

This application is a U.S. National Phase Application under 35 U.S.C. §371 of International Patent Application PCT/RU2010/000292 filed Jun. 4, 2010, which claims priority to Russian Patent Application No. 2009137333 filed Oct. 8, 2009. The International Application was published on Apr. 14, 2011, as International Publication No. WO 2011/043690A1 under PCT Article 21(2). The entire contents of these applications are hereby incorporated by reference.

TECHNICAL FIELD

The inventions relate to antiseptic agents and the method for producing thereof and can be used as a broad-spectrum disinfectant in medicine, veterinary medicine, agriculture etc.

According to contemporary notions, the main reason behind spoilage of almost all materials (wood, metal, leather, paint, plaster, food products etc.), the majority of diseases of humans, animals and plants is the activity of germs—bacteria, fungi, viruses and protozoans. The battle against microbes is becoming more and more urgent in all industries, in medicine, veterinary medicine and agriculture. Antiseptics are the most important means of preventing propagation of microbial damages in all types of industries. The number of publicly available antiseptics for industrial applications, medicine, veterinary medicine and agriculture is clearly insufficient. The majority of existing products have a number of significant disadvantages, the principal among them being toxicity, unpleasant odor and low effectiveness. The development and propagation of germs that are resistant to existing antibiotics is observed everywhere (Fidel P. L. Jr, Vazquez J. A., Sobel J. D. *Candida glabrata*: review of epidemiology, pathogenesis and clinical disease with comparison to *C. albicans* 1999, 1:80-96. White T. Antifungal drug resistance in *Candida albicans*, ASM News 8:427-433). Many industrial antiseptics are by-products of petrochemical processing and—therefore—toxic, have a strong odor or contain an increased amount of metals, e.g. copper, which also constitutes a serious disadvantage.

Nowadays there is a demand for new antiseptics, especially in light of constant changes of the species composition of pathogenic microflora and the emergence of forms that are resistant to existing antiseptics. Usually the research is directed at obtaining antiseptics with predetermined physicchemical characteristics (solubility, hydrolytic stability) and biological properties (scope of action, specificity regarding various microorganisms, activity towards antibiotic-resistant strains etc.).

BACKGROUND ART

A known method for producing of biocidal guanidine uses condensation polymerization of a mixture of hexamethylenediamine, dodecamethylenediamine and guanidine hydrochloride. When the process of condensation polymerization is completed, a 3-excess of hydrazine hydrate is added to the solution of the obtained copolymer and then the solution is heated (by means of reflux condenser until no more ammonia is produced).

The solution is then vacuum-dried, mixed with 1 mole of isonicotinic acid and heated by means of an oil bath at 150° C. until no more moisture is produced, see RU 2176523 C1.

The obtained product is hydrophobic polyguanidine; its aqueous solution is a biocidal agent intended for use as a disinfectant for tuberculosis.

Treatment of the obtained polyguanidine with hydrazine doesn't allow introducing a hydrazine unit into the polymer chain, since the polymer chain either fails to break (during brief heating) or becomes completely destroyed (during prolonged and/or more intense heating). In any case the chain cannot be preserved while introducing a hydrazine unit thereto during implementation of the method according to RU 2176523 C1. Biocidal polyguanidine obtained according to this method has low biological activity and a narrow spectrum of activity.

Another method for producing biocidal polyguanidine comprises condensation polymerization of α,ω-diamine with guanidine salt; the method uses hydrophobic α,ω-diamine mixed with hexamethylenediamine or with 4,9-dioxa-dodecadimine $H_2N-(CH_2)_3-O-(CH_2)_4-O-(CH_2)_3-NH_2$ at the following ratios, mass %:

hydrophobic α,ω-diamine 16-60 hexamethylenediamine or 4,9-dioxa-dodecadimine 84-40, wherein 1,10-decamethylenediamine $H_2N-(CH_2)_{10}-NH_2$ or 1,12-dodecamethylenediamine $(H_2N-(CH_2)_{12}-NH_2$ or N,N-bis-(3-aminopropyl)dodecylamine is used as hydrophobic α,ω-diamine

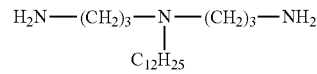

Implementation of the method allows obtaining biocidal polyguanidine with the following formula:

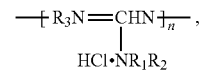

where n=30-50;

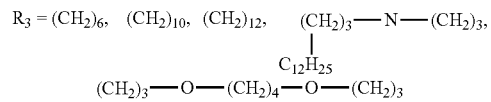

$R_1$ and $R_2$=H, $CH_3$, $C_2H_5$, $C_4H_9$, $C_8H_{17}$, $CH_2C_6H_5$, RU 2324478 C2.

This method (RU 2324478 C2), which was taken as a prototype of the current invention, does not provide a sufficient degree of polymerization of input components (n=30-50) and does not allow obtaining a biocidal agent with high level of biological activity.

Biocidal polyguanidines of the abovementioned type ("metacide" and analogous solutions) have been in use for more than 50 years, which led to the emergence of a large number of diverse resistant strains of pathogenic microorganisms.

SUMMARY OF THE INVENTIONS

It is an object of the current inventions to obtain a biocidal polyguanidine with high level of broad-spectrum antimicrobial activity.

According to the invention, the inventive method for producing of biocidal polyguanidine that comprises condensation polymerization of hexamethylenediamine with guanine salt additionally uses hydrazine hydrate during the condensation polymerization process, at the following ratio of components, mass %:

hexamethylenediamine 20-55
guanidine salt 25-65
hydrazine hydrate the rest.

According to the invention, the inventive substance is biocidal polyguanidine obtained by means of the method as claimed in claim 1, with the following formula:

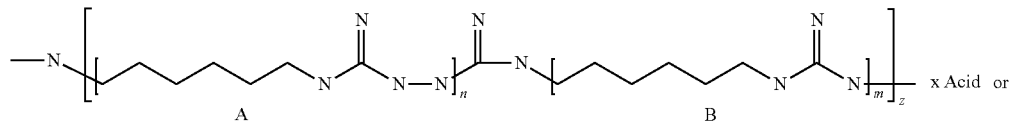

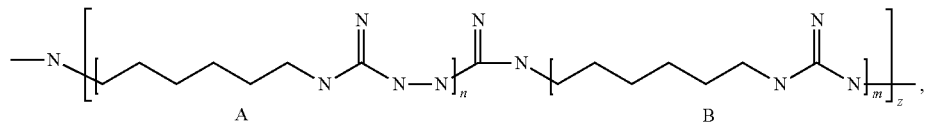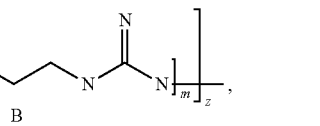

where
n—the number of links A in a single unit of the polymer chain, n=1-3;
m—the number of links B in a single unit of the polymer chain, m=2-10;
z—the number of single units in the polymer chain, z=4-20;

Acid—an acid.

The applicant has not found any sources of information containing data on engineering solutions identical to this invention, which enables to conclude that the invention conforms to the criterion "Novelty" (N).

The applicant has not found any sources of information containing data on the influence of the features of the invention on the technical result produced by the invention, which enables to conclude that the invention conforms to the criterion "Inventive Step" (IS).

BRIEF DESCRIPTION OF THE DRAWINGS

The inventions are further explained, by way of detailed description of examples of their embodiments, without reference to any drawings.

PREFERRED EMBODIMENT

The process of obtaining biocidal polyguanidine by means of the inventive method is explained by way of examples.

Example 1

A 1 l flask provided with a gas outlet pipe and a thermometer was loaded with 95.5 g of guanidine hydrochloride (48.7 mass %), 95.5 g of hexamethylenediamine (48.7 mass %) and 5 g of hydrazine hydrate (2.6 mass %). The contents of the flask were stirred and placed into an air bath, while the gas outlet pipe was connected to the receiver for collecting ammonia; the reaction mixture was heated to 200° C. with gradual stripping of water and ammonia and was sustained at this temperature for 2 hours until no more ammonia was produced. Then this hot and syrupy mass was poured onto a metal tray and cooled, thus obtaining 179 g of the product as a solid, almost colorless transparent glassy substance with the following formula:

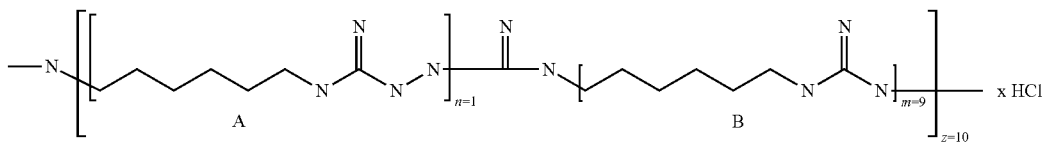

Total number of links A and B in an average polymer chain (n+m)z=100.

Example 2

The method was implemented in the same way as in example 1 using the following components, mass %:
Guanidine hydrochloride 65
Hexamethylenediamine 20
Hydrazine hydrate 15

The obtained substance has the following formula:

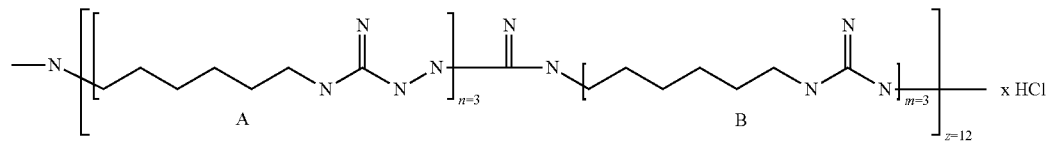

Total number of links A and B in an average polymer chain $(n+m)z=60$.

Example 3

The method was implemented in the same way as in example 1 using the following components, mass %:
Guanidine hydrochloride 40
Hexamethylenediamine 55
Hydrazine hydrate 5.5
The obtained substance has the following formula:

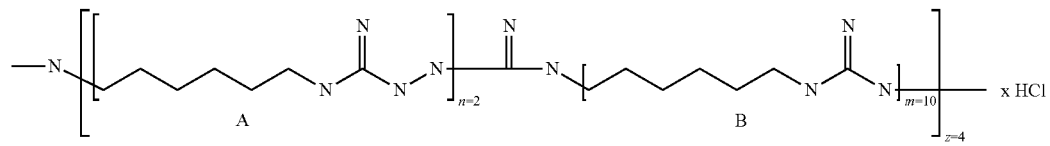

Total number of links A and B in an average polymer chain $(n+m)z=48$.

Example 4

The method was implemented in the same way as in example 1 using the following components, mass %:
Guanidine sulphate 50
Hexamethylenediamine 45
Hydrazine hydrate 5
The obtained substance has the following formula:

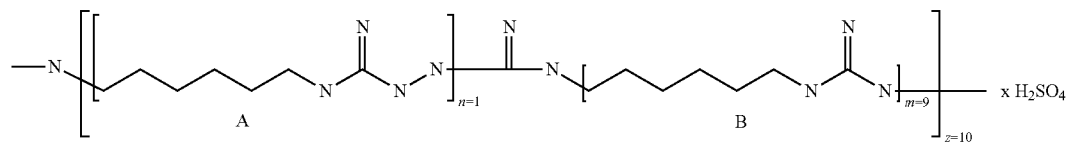

Total number of links A and B in an average polymer chain $(n+m)z=100$.

Example 5

The method was implemented in the same way as in example 1 using the following components, mass %:
Guanidine carbonate 50
Hexamethylenediamine 45
Hydrazine hydrate 5
The obtained substance has the following formula:

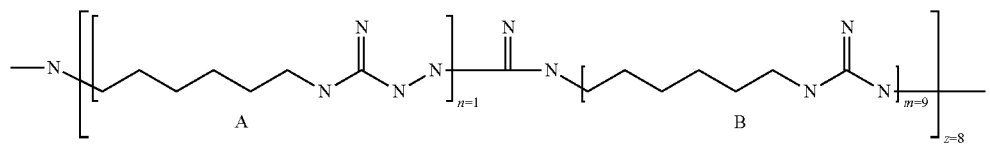

Total number of links A and B in an average polymer chain $(n+m)z=80$.

Example 6

The method was implemented in the same way as in example 1 using the following components, mass %:
Guanidine acetate 50
Hexamethylenediamine 37.5
Hydrazine hydrate 12.5
The obtained substance has the following formula:

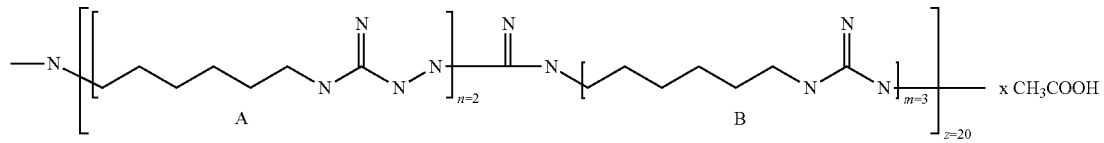

Total number of links A and B in an average polymer chain $(n+m)z=100$.

Example 7

The method was implemented in the same way as in example 1 using the following components, mass %:
Guanidine benzoate 64.3
Hexamethylenediamine 33.9
Hydrazine hydrate 1.8
The obtained substance has the following formula:

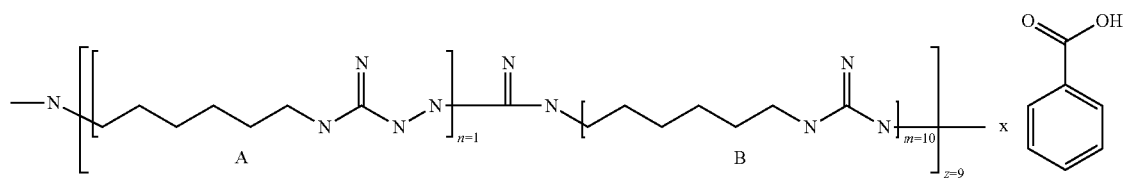

Total number of links A and B in an average polymer chain $(n+m)z=99$.

Element compositions of the substances from examples 1-7 that were obtained according to the inventive method are shown in Table 1.

Antimicrobial activity of the inventive substance according to examples 1-7, as compared with the prototype, is confirmed by the following examples.

Example 8

Assessment of Antifungal Activity of the Inventive Substance Towards Spores of Fungi Various fungi were used in the experiments—vegetative forms and spores that cause diseases in humans and animals, and also spoil agricultural products and various industrial materials—wood, leather etc.

Biocidal properties were tested on spores of fungi cultures stipulated by standard GOST 9.050-75. Optical density of the inoculating suspension of spores E=0.310. Suspension contained equal proportions of spores of the following micromycetes:
*Aspergillis niger*
*Aspergillis terreus*
*Alternaria alternate*
*Fusarium moniliforme*
*Penicillium brevicompactum*
*Penicillium chrysogenum*
*Penicillium ochro-chloron*

*Penicillium martensii*
*Trichoderma viride*

Assessment of antiseptic properties of the inventive substances was done after 7 days of cultivation of micromycetes by means of the paper-disk method and the well method (see Table 2).

The area of inhibition was from 16 to 38 mm. The substance from examples 3 and 4 demonstrated biocidal properties in a concentration as low as 0.1%.

Example 9

Assessment of the Effect of the Substance Upon Yeast and Yeast-Like Fungi

Activity against yeast and yeast-like fungi was determined by means of the serial dilution method.

The tested substances were diluted in water and titrated in medium N-1, RPMI, sabouraud so that the inventive substance contained in separate test tubes with medium would have different concentration values.

Data shown in Table 3 indicate a very high activity of the inventive substance against yeast and unicellular fungi of *Candida* genus as compared with the prototype.

Example 10

Assessment of Effectiveness of the Substance Against Gram-Positive and Gram-Negative Bacteria (Aerobic and Anaerobic)

Standard collective strains and bacteria isolated from patients were used in the experiments. Assessment was done by means of the serial dilution method, using culture media suitable for cultivating corresponding types of microorganisms.

Compounds were diluted in sterile water and titrated at concentrations from 500 to 0.025 mg/l. Concentration of the agent in the medium of adjacent test tubes had a twofold difference. The results were assessed after a 72-hour cultivation of the bacteria at 37° C. (see Table 4).

Thus, the inventive substance has a pronounced antibacterial activity.

Example 10

Assessment of the Effect of the Inventive Substance Upon *Mycobacteria Tuberculosis*

The activity was assessed on the basis of the standard strain *Mycobacterium tuberculosis* H37Rv that is susceptible to all antimicrobial agents. Assessment of the antimicrobial effect was done by means of the serial dilution method.

Substances were diluted in sterile water and titrated, so that the compound in different test tubes with medium would have concentrations from 200 to 0.025 mg/l. Concentration of the compound in the medium of adjacent test tubes had a twofold difference. The results were assessed after a 72-hour cultivation of the bacteria at 37° C. (see Table 5).

Thus, the activity of the inventive compounds against tuberculosis agent is significantly higher than that of the prototype.

Example 11

Assessment of the Antiprotozoal Activity of the Substance Against Trichomonads (*Trichomonas vaginalis*)

Strains isolated from patients were used in the experiments. Assessment was done by means of the serial dilution method, using culture media suitable for cultivating corresponding types of microorganisms.

Substances were diluted in sterile water and titrated at concentrations from 500 to 0.025 mg/l. Concentration of the compound in the medium of adjacent test tubes had a twofold difference. The results were assessed after a 72-hour cultivation of the bacteria at 37° C. (see Table 6).

The results indicate a rather high activity of the inventive substance against protozoans, with trichomonads as an example.

Example 12

Assessment of Effect of the Inventive Substance Upon Herpes Simplex Virus

Antiviral activity was studied on the basis of herpes simplex virus of type I (VPG-I/Leningrad/248/88) by means of the conventional method [Gentry G. A., Lawrency N., Lushbaugh N. Isolation and differentiation of Herpes simplex virus and *Trichomonas vaginalis* in cell culture, J. of Clinical Microbiology 1985, Vol. 22, No. 2, P. 199-204]. The viruses were cultivated on the basis of passaged culture of Vero cells obtained from the bank of cell cultures of Cytology Institute of RAN (Russian Academy of Science). The results were assessed according to the presence of cytopathogenic effect of the virus against cells after 36 hours of cultivation under 37° C. in a $CO_2$-incubator. The number of unchanged cells was calculated in order to assess the cytopathic effect of the virus. Results are shown in Table 7.

The results indicate that the inventive substance is highly active against herpes virus.

Example 13

Using the Inventive Substance to Combat a Mixed Microbial Infection

Laboratory animals (guinea pigs) had a part of their hair coat shaved and surface scratches inflicted upon them, and then had a microbial mixture applied (rubbed in) containing fungi of *Candida* genus, staphylococcus, *Escherichia coli* and enterococcus. 24 hours later all animals had a local inflammation. Treatment was delivered through an ointment that was prepared from the substance according to example 3 or, alternatively, the prototype substance prepared as a lanolin-based ointment. 100 µg/ml of the substances were added. Animals in the control group were treated with pure lanolin. Each group consisted of 5 animals. The measure of effectiveness was the time until complete healing and regeneration of skin. In groups that received treatment by substance from example 3, the healing was achieved after 5 days. In groups that received the prototype agent during 6 days, all animals were sick. This group recovered after 13 days, and the lanolin control group recovered after 15 days.

The obtained results show that the inventive substance can be effectively used as a local treatment for mixed infections caused by gram-positive and gram-negative bacteria and fungi.

Example 14

Using the Inventive Substance to Impart Antibacterial Properties to Paints

The example used white water-emulsion paint manufactured by factory "Kronos", adding to the paint the inventive substance from example 5 in final concentration of 1.0%.

Culture medium in Petri dishes was inoculated with test microbes (*E. coli* ATSS 25922, *S. aureus* VT209, *Candida* ATSS 885-653, *Aspergillus niger* VT-7765), slightly dried for 15 minutes and then covered by paper disks with diameter of 5 mm that were saturated with paint containing the inventive substance. After incubating for 20-24 hours at 35-37° C., the presence and size of the area of microbe growth inhibition around the disks was determined. All experiments showed pronounced inhibition of growth of test strains of the bacteria that were used.

Thus, the obtained data indicate that the inventive substance introduced into water-emulsion paint retained its antimicrobial properties and manifested them against various unrelated bacteria and fungi.

Example 15

Using the Inventive Substance to Treat Root Canals of Teeth

The study used extirpated teeth. Prior to the experiment, the teeth were processed, foreign substances were removed and the root canals were cleaned. Then 0.05% aqueous solution of the substance from example 7 or the prototype substance was introduced into the canals of treated teeth, whereupon the entrance to the canal was sealed by means of a temporary liquid-tight filling. A tooth was placed in a sterile and empty Petri dish into an air bath for 24 hours and then incubated at 37° C. for 20-24 hours. During the incubation the substance could diffuse into dentinal tubules. It is a known fact that dentinal tubules could be the place where harmful and dangerous microbes remain after the root canals are treated; total length of the tubules in a single-root tooth amounts to about 5 kilometers. After incubation the teeth were placed in semiliquid agar that contained test microbes (*E. coli* or *S. aureus*) in the amount of 1.0–5.0×105 ml.

Dishes were incubated for additional 20-24 hours at 37° C. The result was assessed according to the presence and size of the growth inhibition area that was formed along the perimeter of the tooth. The presence of a growth inhibition area indicated that the agent penetrated dentin, was able to emerge along the perimeter of the tooth (in human organism into the tissues around the tooth) and retain its antimicrobial properties.

The agent produced antimicrobial effect in the conducted experiments at all tested concentrations, starting from 0.05.

Example 16

Imparting Antimicrobial Properties to Suture Material and Endoprostheses

Pieces of threads about 1 cm long were placed into Petri dishes Ø 90 mm with a thin (3 mm) substrate made of 1.5% meat peptone agar (MPA); 2 pieces of thread per sample, 4 pieces per dish. Samples were covered with 6 ml of 0.7% MPA that contained 0.6 ml of the test culture at concentration of 5×105 microorganisms per 1 ml. Inoculations were incubated in an air bath at 37° C. during 24 hours (bacteria), 30° C. 24 hours (fungi).

Dishes with 1.5% MPA were lawn-inoculated with a suspension of microorganisms in physiological saline at concentration of 5×105, diluted in tenfold for bacteria/5 units, diluted in tenfold for fungi. Dishes were dried at room temperature during 10-15 minutes, then they were covered by disks made of filter paper Ø 6 mm saturated with the solutions under study, 2 disks per sample, 4 disks per dish. Samples were again dried in an upside down position for 10-15 minutes and incubated in an air bath at 37° C. for 24 hours (bacteria), at 30° C. for 24 hours (fungi).

The results were assessed according to the presence or absence of growth inhibition areas around the tested subjects (see Table 8); suture threads and meshes were used (endoprostheses).

The obtained results indicate that the inventive substance (according to example 2) placed upon suture material is washed off while retaining its broad-spectrum antimicrobial activity and inhibiting the growth of gram-positive and gram-negative bacterial flora, as well as unicellular and multicellular fungi that pose a threat for humans.

INDUSTRIAL APPLICABILITY

The inventions can be implemented by means of known materials and equipment. In applicant's opinion, this enables to conclude that the inventions conform to the criterion "Industrial Applicability" (IA).

Element Compositions of the Substances from Examples 1-7

TABLE 1

| Example No | ×Acid | n | m | z | C | H | N | Cl(S) |
|---|---|---|---|---|---|---|---|---|
| 1 | HCl | 1 | 9 | 10 | 46.91 | 9.06 | 24.25 | 19.78 |
| 2 | HCl | 3 | 2 | 12 | 45.05 | 9.12 | 26.27 | 19.56 |
| 3 | HCl | 2 | 10 | 4 | 46.60 | 9.20 | 23.97 | 20.23 |
| 4 | $H_2SO_4$ | 1 | 9 | 10 | 43.60 | 9.02 | 22.11 | 8.44 |
| 5 | not | 1 | 9 | 8 | 58.0 | 10.67 | 30.45 | — |
| 6 | $CH_3COOH$ | 2 | 3 | 20 | 45.87 | 8.69 | 21.94 | — |
| 7 | $C_6H_5COOH$ | 1 | 10 | 9 | 63.26 | 8.71 | 15.91 | — |

Column header note: Data of the element analysis, %

Results of Assessment of Antiseptic Properties of Inventive Substances

TABLE 2

| Spores of fungi (mixture) | Minimal overwhelming (biocidal) concentration substances in a water solution, mkg/ml | | | | | | | |
| | 1 | 2 | 3 | 4 | 5 | 6 | 7 | Prototype |
|---|---|---|---|---|---|---|---|---|
| A. niger | 1.0 | 1.5 | 0.5 | 0.5 | 1.0 | 1.5 | 2.0 | 3.5 |
| A. terreus | | | | | | | | |
| A. alternata | | | | | | | | |
| F. moniliforme | | | | | | | | |
| P. brevicompactum | | | | | | | | |
| P. chrysogenum | | | | | | | | |
| P. ochrochloron | | | | | | | | |
| P. martensii | | | | | | | | |

Efficiency of Substance Against Gram-Positive and Gram-Negative Bacteria

TABLE 3

| Fungi | Strain | Minimal overwhelming concentration, mkg/ml (Examples 1-7 and prototype) | | | | | | | |
| | | 1 | 2 | 3 | 4 | 5 | 6 | 7 | Prototype |
|---|---|---|---|---|---|---|---|---|---|
| Saccharomyces cervisiae | VT-2 | 0.5 | 0.7 | 0.4 | 0.5 | 0.5 | 0.7 | 0.8 | 12000 |

TABLE 3-continued

Minimal overwhelming concentration, mkg/ml
(Examples 1-7 and prototype)

| Fungi | Strain | 1 | 2 | 3 | 4 | 5 | 6 | 7 | Prototype |
|---|---|---|---|---|---|---|---|---|---|
| Candida albicans | 21 | 0.8 | 0.7 | 0.5 | 0.5 | 0.7 | 0.8 | 0.9 | 10000 |
| Candida albicans | 372 | 0.9 | 0.7 | 0.3 | 0.3 | 0.6 | 0.9 | 1.0 | 12000 |
| Candida albicans | 80 | 1.0 | 0.8 | 0.3 | 0.4 | 0.5 | 0.6 | 0.7 | 12000 |
| Candida glabrata | 382 | 0.8 | 0.8 | 0.7 | 0.8 | 1.0 | 1.1 | 1.2 | 14000 |
| Candida glabrata | 111 | 0.7 | 0.8 | 0.5 | 0.6 | 0.7 | 0.8 | 0.9 | 12000 |
| Candida glabrata | 160 | 0.8 | 0.9 | 0.6 | 0.7 | 0.8 | 0.8 | 1.0 | 12000 |
| Candida krusei | 21 | 0.9 | 1.0 | 0.7 | 0.8 | 1.0 | 1.1 | 1.2 | 12000 |

Efficiency of Substance Against Gram-Positive and Gram-Negative Bacteria (Aerobic and Anaerobic)

TABLE 4

| Microorganism | Minimal overwhelming concentration, mkg/ml | | | | | | | |
|---|---|---|---|---|---|---|---|---|
| | 1 | 2 | 3 | 4 | 5 | 6 | 7 | Prototype |
| Escherichia coli ATCC922 | 0.7 | 0.9 | 0.5 | 0.5 | 1.0 | 1.5 | 2.0 | 2.0 |
| Salmonella typhimur. VT-191 | 1.5 | 2.0 | 1.0 | 1.1 | 2.0 | 3.0 | 4.0 | 10.1 |
| Enterococcus fecalis | 1.5 | 2.0 | 1.0 | 1.5 | 2.0 | 2.5 | 3.0 | 4.0 |
| Pseudomonas aeruginosa ATCC27853 | 0.1 | 0.2 | 0.1 | 0.1 | 0.1 | 0.1 | 0.2 | 0.1 |
| Klebsiella pneumoniae | 0.7 | 1.0 | 0.5 | 1.0 | 1.5 | 1.5 | 2.0 | 2.0 |
| Bacillus cereus | 2.5 | 3.0 | 2.0 | 2.0 | 2.5 | 2.5 | 3.0 | 12 |
| Staphylococcus aureus VT-209 | 2.5 | 3.0 | 2.0 | 2.5 | 2.5 | 3.0 | 3.0 | 5.0 |
| Fusobacterium nucleatum | 0.3 | 0.4 | 0.2 | 0.3 | 0.5 | 0.6 | 0.7 | 0.4 |
| Porfhiromonas gingivalis | 0.8 | 1.0 | 0.5 | 0.6 | 1.0 | 1.5 | 2.5 | 6.0 |
| Prevotella melaninogenica | 0.8 | 1.0 | 0.4 | 0.7 | 1.0 | 1.1 | 1.4 | 1.5 |

Efficiency of Substance Against *Mycobacterium tuberculosis*

TABLE 5

| Microorganism | Minimal overwhelming concentration, mkg/ml | | | | | | | |
|---|---|---|---|---|---|---|---|---|
| | 1 | 2 | 3 | 4 | 5 | 6 | 7 | Prototype |
| Mycobacterium tuberculosis H37Rv | 10.0 | 10.0 | 10.0 | 10.0 | 10.0 | 10.0 | 10.0 | 2000 |

Antiprotozoal Activity of the Substance Against Trichomonads (*Trichomonas Vaginalis*)

TABLE 6

| Microorganism | Minimal overwhelming (bactericidal) concentration, mkg/ml | | | | | | | |
|---|---|---|---|---|---|---|---|---|
| | 1 | 2 | 3 | 4 | 5 | 6 | 7 | Prototype |
| Trichomonas vaginalis | 0.02 | 0.02 | 0.01 | 0.01 | 0.01 | 0.02 | 0.02 | 0.02 |

Efficiency of the Inventive Substance Upon Herpes Simplex Virus

TABLE 7

| Virus | Minimal overwhelming concentration, mkg/ml | | | | | | | |
|---|---|---|---|---|---|---|---|---|
| | 1 | 2 | 3 | 4 | 5 | 6 | 7 | Prototype |
| VPG-I/Leningrad//248/88 | 80.0 | 100.0 | 50.0 | 70.0 | 100.0 | 140.0 | 150.0 | 1000 |

Antimicrobial Properties to Suture Material and Endoprostheses

| No | Tested object | Antimicrobial activity (mm from edge of a string) test cultures | | | |
|---|---|---|---|---|---|
| | | E. coli ATCC 25922 | St. aureus 209 | Candida ATCC 885-653 | Aspergillus niger |
| 1 | Kapron string processed by a water solution of the inventive substance (1.0 mg/1.0 ml) | 4 | 6 | 5 | 6 |
| 2 | Lavsan string processed by a water solution of the inventive substance (1.0 mg/1.0 ml) | 5 | 4 | 4 | 5 |
| 3 | Propylene grid from the inventive substance (1.0 mg/1.0 ml) | 5 | 6 | 5 | 4 |
| 4 | Grid from the PVDF fiber inventive substance (1.0 mg/1.0 ml) | 6 | 5 | 5 | 3 |
| 5 | Lavsan string from the inventive substance (1.0 мг/1.0 мл) | 8 | 7 | 8 | 6 |

The invention claimed is:

1. A method for producing a polyguanidine comprising reacting hexamethylenediamine with a guanidine salt and hydrazine hydrate, wherein the mass % ratio of said hexamethylenediamine, guanidine salt, and hydrazine hydrate is:

Hexamethylenediamine 20-55

Guanidine salt 25-65

Hydrazine hydrate the balance, wherein the mass % of hydrazine hydrate is greater than 0.

2. A polyguanidine having the following formula:

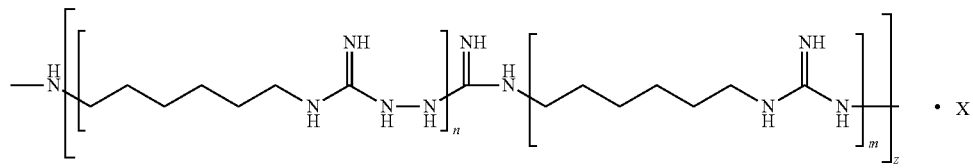

wherein:
n=1-3;
m=2-10;
z=4-20; and
X is absent or an acid.

3. The method of claim 1, wherein said reacting is conducted under condensation polymerization reaction conditions.

4. The method of claim 1, wherein said reacting comprises forming a mixture of said hexamethylenediamine, guanidine salt, and hydrazine hydrate and heating the mixture to a temperature of about 200° C.

5. The method of claim 1, wherein the mass % ratio of said hexamethylenediamine, guanidine salt, and hydrazine hydrate is 48.7:48.7:2.6.

6. The method of claim 1, wherein the mass % ratio of said hexamethylenediamine, guanidine salt, and hydrazine hydrate is 20:65:15.

7. The method of claim 1, wherein the mass % ratio of said hexamethylenediamine, guanidine salt, and hydrazine hydrate is 55:40:5.5.

8. The method of claim 1, wherein the mass % ratio of said hexamethylenediamine, guanidine salt, and hydrazine hydrate is 45:50:5.

9. The method of claim 1, wherein the mass % ratio of said hexamethylenediamine, guanidine salt, and hydrazine hydrate is 37.5:50:12.5.

10. The method of claim 1, wherein the mass % ratio of said hexamethylenediamine, guanidine salt, and hydrazine hydrate in said mixture is 33.9:64.3:1.8.

11. The method of claim 1, wherein the guanidine salt is selected from the group consisting of: guanidine hydrochloride, guanidine sulphate, guanidine carbonate, guanidine acetate, and guanidine benzoate.

12. A polyguanidine produced by the method of claim 1.

13. The polyguanidine of claim 2, having the structure:

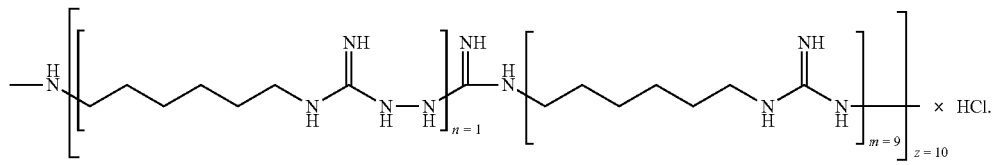

14. The polyguanidine of claim 2, having the structure:

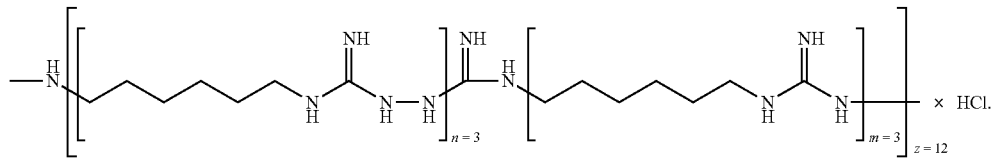

15. The polyguanidine of claim 2, having the structure:

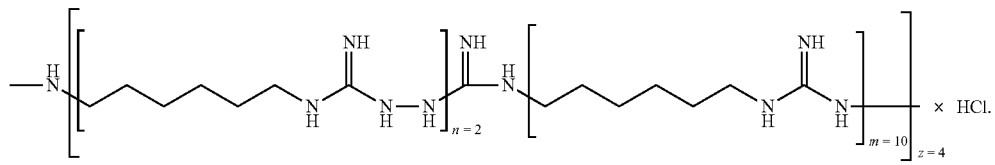

16. The polyguanidine of claim 2, having the structure:

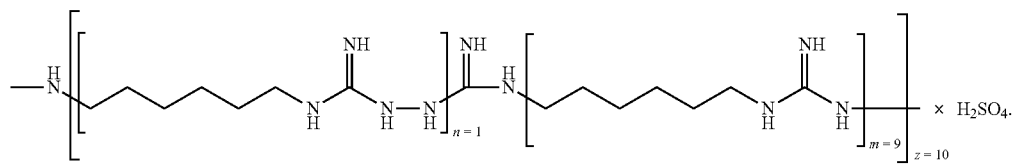

17. The polyguanidine of claim 2, having the structure:

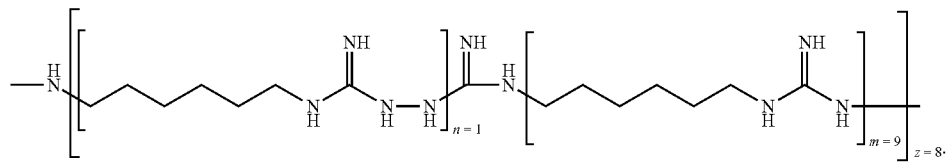

18. The polyguanidine of claim 2, having the structure:

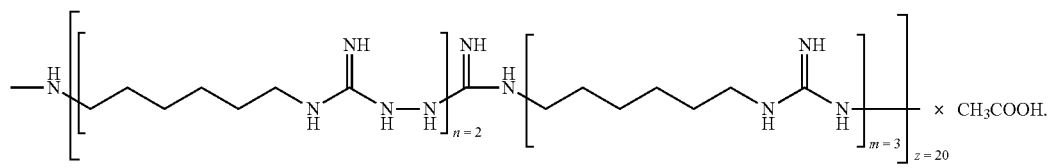

19. The polyguanidine of claim 2, having the structure:

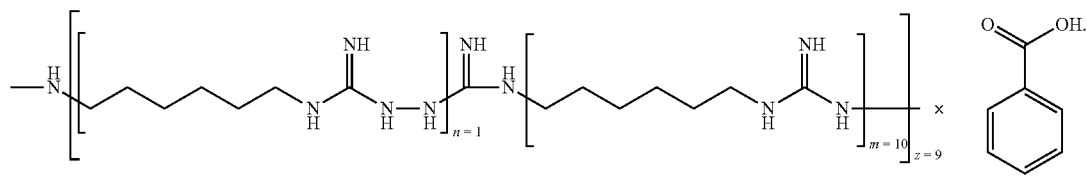

20. A composition comprising the polyguanidine of claim 2 and a carrier or excipient.
21. The composition of claim 20, which is a solution.
22. The composition of claim 20, which is an ointment.
23. The composition of claim 20, which is an antiseptic or disinfectant composition.
24. A biomedical material comprising the polyguanidine of claim 2.
25. The biomedical material of claim 24 which is selected from the group consisting of endoprosthesis, mesh, suture, and dental materials.
26. A paint comprising the polyguanidine of claim 2.
27. A method for preventing and/or inhibiting growth of an agent selected from the group consisting of bacterial, fungal, viral, and protozoal agents comprising administering an effective amount of the polyguanidine of claim 2.
28. A method for preventing and/or treating an infection in a subject in need thereof comprising administering to the subject an effective amount of the polyguanidine of claim 2.
29. The method of claim 28, wherein the infection is caused by an agent selected from the group consisting of bacterial, fungal, viral, and protozoal agents.
30. The method of claim 28, wherein the infection is a mixed infection.
31. The method of claim 28, wherein the infection is a systemic infection.
32. The method of claim 28, wherein the infection is a dental infection.
33. The method of claim 28, wherein the infection is a skin infection or an infection of a wound.
34. The method of claim 28, wherein the infection is a mucosal infection.
35. The method of claim 28, wherein the compound is administered topically.
36. The method of claim 28, wherein the compound is administered locally.

* * * * *